United States Patent
Santello et al.

(10) Patent No.: US 10,932,688 B2
(45) Date of Patent: Mar. 2, 2021

(54) EEG-BASED DECODING AND CLOSED-LOOP NEUROMODULATION SYSTEM FOR ASSESSING AND ENHANCING SENSORIMOTOR LEARNING

(71) Applicants: Marco Santello, Gilbert, AZ (US); Justin Fine, Phoenix, AZ (US)

(72) Inventors: Marco Santello, Gilbert, AZ (US); Justin Fine, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 355 days.

(21) Appl. No.: 16/124,472

(22) Filed: Sep. 7, 2018

(65) Prior Publication Data
US 2019/0069796 A1 Mar. 7, 2019

Related U.S. Application Data

(60) Provisional application No. 62/555,488, filed on Sep. 7, 2017.

(51) Int. Cl.
*A61B 5/0482* (2006.01)
*A61B 5/0478* (2006.01)
(Continued)

(52) U.S. Cl.
CPC ........ *A61B 5/0482* (2013.01); *A61B 5/04012* (2013.01); *A61B 5/0476* (2013.01);
(Continued)

(58) Field of Classification Search
CPC ... A61B 5/0476; A61B 5/4076; A61B 5/4012; A61B 5/11; A61B 5/0482; A61B 5/0478; A61B 5/6814; G06F 3/015
See application file for complete search history.

(56) References Cited

U.S. PATENT DOCUMENTS

| | | | |
|---|---|---|---|
| 6,996,261 B2 | 2/2006 | deCharms | |
| 2014/0277582 A1* | 9/2014 | Leuthardt | A61F 2/72 623/25 |

(Continued)

FOREIGN PATENT DOCUMENTS

| | | |
|---|---|---|
| WO | 2015172096 A1 | 11/2015 |
| WO | 2017147041 A1 | 8/2017 |
| WO | 2018057898 A1 | 3/2018 |

OTHER PUBLICATIONS

Alegre et al., "Beta electroencephalograph changes during passive movements: sensory afferences contribute to beta event-related desynchronization in humans," Neuroscience Letters (2002) 331(1), 29-32.

(Continued)

*Primary Examiner* — Christine H Matthews
*Assistant Examiner* — Joshua Daryl D Lannu
(74) *Attorney, Agent, or Firm* — Michael Best & Friedrich LLP

(57) ABSTRACT

Systems and methods are described for enhancing sensorimotor learning using EEG decoding and closed-loop neuromodulation. A plurality of EEG electrodes and a plurality of stimulation electrodes are coupled to a learning subject. An output device of an adaptive learning system provides a sequence of instructions to the learning subject for performing a sensorimotor task in accordance with a defined learning schedule. The defined learning schedule is adjusted based on a monitored EEG signal while performing the task and, in some implementations, a neuromodulation stimulus signal is applied to the learning subject that is designed to cause the monitored EEG signal of the learning subject to approach at least one target EEG signal parameter.

14 Claims, 2 Drawing Sheets

(51) Int. Cl.
 A61B 5/04 (2006.01)
 G06F 3/01 (2006.01)
 A61B 5/0476 (2006.01)
 A61B 5/00 (2006.01)
 A61B 5/11 (2006.01)
(52) U.S. Cl.
 CPC .......... *A61B 5/0478* (2013.01); *A61B 5/4076* (2013.01); *G06F 3/015* (2013.01); *A61B 5/11* (2013.01); *A61B 5/6814* (2013.01)

(56) References Cited

U.S. PATENT DOCUMENTS

| | | | |
|---|---|---|---|
| 2016/0140865 | A1 | 5/2016 | Marzetti et al. |
| 2017/0193546 | A1* | 7/2017 | Bennett .............. G06Q 30/0201 |
| 2017/0265784 | A1 | 9/2017 | Santello |
| 2019/0054277 | A1 | 2/2019 | LaBelle et al. |
| 2019/0167504 | A1 | 6/2019 | Polygerinos et al. |
| 2019/0227632 | A1 | 7/2019 | Santello et al. |

OTHER PUBLICATIONS

Amiez et al., "Anterior cingulate error-related activity is modulated by predicted reward," European Journal of Neuroscience (2005) 21(12), 3447-3452.

Arnal et al., "Cortical oscillations and sensory predictions," Trends in Cognitive Sciences (2012).

Arrighi et al., "EEG theta dynamics within frontal and parietal cortices for error processing during reaching movements in a prism adaptation study altering visuo-motor predictive planning," PLoS ONE (2016) 11(3).

Baker, "Oscillatory interactions between sensorimotor cortex and the periphery," Current Opinion in Neurobiology (2007).

Behrens et al., "Learning the value of information in an uncertain world," Nature Neuroscience (2007) 10(9).

Bonnefond et al., "Communication between Brain Areas Based on Nested Oscillations," eNeuro (2017) 0153-16.

Brashers-Krug et al., "Consolidation in human motor memory," Nature (1996) 382(6588), 252-5.

Brittain et al., "Oscillations and the basal ganglia: Motor control and beyond," NeuroImage (2014).

Caithness et al., "Failure to consolidate the consolidation theory of learning for sensorimotor adaptation tasks," The Journal of Neuroscience: The Official Journal of the Society for Neuroscience (2004) 24(40), 8662-71.

Cavanagh et al., "Frontal theta links prediction errors to behavioral adaptation in reinforcement learning," NeuroImage (2010) 49(4), 3198-3209.

Cavanagh et al., "Prelude to and resolution of an error: EEG phase synchrony reveals cognitive control dynamics during action monitoring," The Journal of Neuroscience (2009) 29(1), 98-105.

Cohen et al., "Cortical electrophysiological network dynamics of feedback learning," Trends in Cognitive Sciences (2011).

Cohen et al., "Midfrontal conflict-related theta-band power reflects neural oscillations that predict behavior," Journal of Neurophysiology (2013) 110(12), 2752-2763.

Cohen, "A neural microcircuit for cognitive conflict detection and signaling," Trends in Neurosciences (2014) 37(9).

Contreras-Vidal et al., "Independent component analysis of dynamic brain responses during visuomotor adaptation," NeuroImage (2004) 21(3), 936-945.

Delorme et al., "EEGLAB: An open source toolbox for analysis of single-trial EEG dynamics including independent component analysis," Journal of Neuroscience Methods (2004)134(1), 9-21.

Diedrichsen et al., "Use-dependent and error-based learning of motor behaviors," The Journal of Neuroscience (2010) 30(15), 5159-66.

Donchin et al., "Quantifying generalization from trial-by-trial behavior of adaptive systems that learn with basis functions: theory and experiments in human motor control," The Journal of Neuroscience(2003) 23(27), 9032-45.

Engel, "Beta-band oscillations-signalling the status quo," Current Opinion in Neurobiology (2010).

Floyer-Lea, "Changing Brain Networks for Visuomotor Control With Increased Movement Automaticity," Journal of Neurophysiology (2004) 92(4), 2405 LP-2412.

Friston et al., "LFP and oscillations-what do they tell us?," Current Opinion in Neurobiology (2015) 31, 1-6.

Fu et al., "Anticipatory Planning and Control of Grasp Positions and Forces for Dexterous Two-Digit Manipulation," Journal of Neuroscience (2010) 270(45), 26723-26726.

Fu et al., "Learned manipulation at unconstrained contacts does not transfer across hands," PLoS ONE (2014) 9(9).

Fu et al., "Retention and interference of learned dexterous manipulation: interaction between multiple sensorimotor processes," Journal of Neurophysiology (2015)113(1), 144-55.

Galea et al., "Dissociating the roles of the cerebellum and motor cortex during adaptive learning: The motor cortex retains what the cerebellum learns," Cerebral Cortex (2011) 21(8), 1761-1770.

Gentili et al., "Cerebral cortical dynamics during visuomotor transformation: adaptation to a cognitive-motor executive challenge," Psychophysiology (2011) 48(6), 813-824.

Gonzalez et al., "Environmental consistency determines the rate of motor adaptation," Current Biology (2014) 24(10), 1050-1061.

Herzfeld et al., "A memory of errors in sensorimotor learning," Science (2014) 345(6202), 1349-1353.

Hirashima et al., "Distinct motor plans form and retrieve distinct motor memories for physically identical movements," Current Biology (2012) 22(5), 432-436.

Huang et al., "Rethinking Motor Learning and Savings in Adaptation Paradigms: Model-Free Memory for Successful Actions Combines with Internal Models," Neuron (2011) 70(4) 787-801.

Imamizu et al., "Explicit contextual information selectively contributes to predictive switching of internal models," Experimental Brain Research (2007) 181(3), 395-408.

Ingram et al., "A single-rate context-dependent learning process underlies rapid adaptation to familiar object dynamics," PLoS Computational Biology (2011) 7(9).

Jenkinson et al., "New insights into the relationship between dopamine, beta oscillations and motor function," Trends in Neurosciences (2011).

Kayser et al., "Principal components analysis of Laplacian waveforms as a generic method for identifying ERP generator patterns: II. Adequacy of low-density estimates," Clinical Neurophysiology (2006) 117(2), 369-380.

Kim et al., "Neural Substrates Related to Motor Memory with Multiple Timescales in Sensorimotor Adaptation," PLoS Biology (2015) 13(12).

Krakauer et al., "Adaptation to Visuomotor Transformations: Consolidation, Interference, and Forgetting," The Journal of Neuroscience (2005) 25(2), 473 LP-478.

Krakauer et al., "Generalization of motor learning depends on the history of prior action," PLoS Biology (2006) 4(10), 1798-1808.

Krakauer et al., "Motor learning and consolidation: The case of visuomotor rotation," Advances in Experimental Medicine and Biology (2009) 629, 405-421.

Lee et al., "Dual Adaptation Supports a Parallel Architecture of Motor Memory," Journal of Neuroscience (2009) 29(33), 10396-10404.

Macdonald et al., "Trial-by-trial variations in subjective attentional state are reflected in ongoing prestimulus EEG alpha oscillations," Frontiers in Psychology (2011) 2.

Miall et al., "Adaptation to rotated visual feedback: A re-examination of motor interference," Experimental Brain Research (2004) 154(2), 201-210.

Murthy et al., "Coherent 25- to 35-Hz oscillations in the sensorimotor cortex of awake behaving monkeys. Proceedings of the National Academy of Sciences of the United States of America," (1992) 89(12), 5670-4.

(56) References Cited

OTHER PUBLICATIONS

Nozaki et al, "Tagging motor memories with transcranial direct current stimulation allows later artificially-controlled retrieval," eLife, 5 (2016).
Osu et al., "Random presentation enables subjects to adapt to two opposing forces on the hand," Nature Neuroscience (2004) 7(2), 111-112.
Pekny et al., Protection and Expression of Human Motor Memories. Journal of Neuroscience (2011) 31(39), 13829-13839.
Pernet et al., "LIMO EEG: A Toolbox for Hierarchical LInear MOdeling of ElectroEncephaloGraphic Data," Computational Intelligence and Neuroscience (2011) 2011(831409).
Pfurtscheller et al., "Event-related EEG/MEG synchronization and desynchronization: Basic principles," Clinical Neurophysiology (1999).
Rousselet et al., "Modeling single-trial ERP reveals modulation of bottom-up face visual processing by top-down task constraints (in some subjects)," Front Psychol (2011) 2:137.
Sedley et al., "Neural signatures of perceptual inference," eLife, 5 (2016).
Shadmehr et al., "Adaptive representation of dynamics during learning of a motor task," Journal of Neuroscience (1994) 14, 3208-3224.
Shadmehr et al., "Neural correlates of motor memory consolidation," Science (1997) 277, 821-825, 277, 821-826.
Sheahan et al., "Motor Planning, Not Execution, Separates Motor Memories," Neuron (2016) 92(4), 773-779.
Sing et al., "Reduction in learning rates associated with anterograde interference results from interactions between different timescales in motor adaptation," PLoS Computational Biology (2010) 6(8).
Smith et al., "Interacting adaptive processes with different timescales underlie short-term motor learning," PLoS Biology (2006) 4(6), 1035-1043.
Swann et al., "Intracranial EEG Reveals a Time- and Frequency-Specific Role for the Right Inferior Frontal Gyrus and Primary Motor Cortex in Stopping Initiated Responses," The Journal of Neuroscience (2009) 29(40), 12675 LP-12685.
Tan et al., "Dynamic neural correlates of motor error monitoring and adaptation during trial-to-trial learning," The Journal of Neuroscience (2014) 34(16), 5678-88.
Tan et al., "Post-Movement Beta Activity in Sensorimotor Cortex Indexes Confidence in the Estimations from Internal Models," The Journal of Neuroscience (2016) 36(5), 1516-28.
Thoroughman et al., "Learning of action through adaptive combination of motor primitives," Nature (2000) 407 (6805), 742-7.
Torrecillos et al., "Distinct Modulations in Sensorimotor Postmovement and Foreperiod β-Band Activities Related to Error Salience Processing and Sensorimotor Adaptation," The Journal of Neuroscience (2015) 35(37), 12753-65.
Tzvi et al., "Reduced alpha-gamma phase amplitude coupling over right parietal cortex is associated with implicit visuomotor sequence learning," NeuroImage (2016) 141, 60-70.
U.S. Appl. No. 16/214,847, filed Dec. 10, 2018 by Santello et al.
Van De Vijver et al., "Frontal oscillatory dynamics predict feedback learning and action adjustment," Journal of Cognitive Neuroscience (2011) 23(12), 4106-4121.
Van Driel et al., "Not All Errors Are Alike: Theta and Alpha EEG Dynamics Relate to Differences in Error-Processing Dynamics," The Journal of Neuroscience (2012) 32(47).
Witney et al., "Learning and decay of prediction in object manipulation," Journal of Neurophysiology (2000) 84(1), 334-43.
Wolpert et al., "Principles of sensorimotor learning," Nature Reviews Neuroscience (2011) 12(12), 739-51.
Womelsdorf et al., "Theta-activity in anterior cingulate cortex predicts task rules and their adjustments following errors," Proceedings of the National Academy of Sciences (2010) 107(11), 5248-5253.
Zhang et al., "Manipulation after object rotation reveals independent sensorimotor memory representations of digit positions and forces," Journal of Neurophysiology (2010) 103(6), 2953-2964.
Zhang et al., "Response preparation and inhibition: The role of the cortical sensorimotor beta rhythm," Neuroscience (2008) 156(1), 238-246.

\* cited by examiner

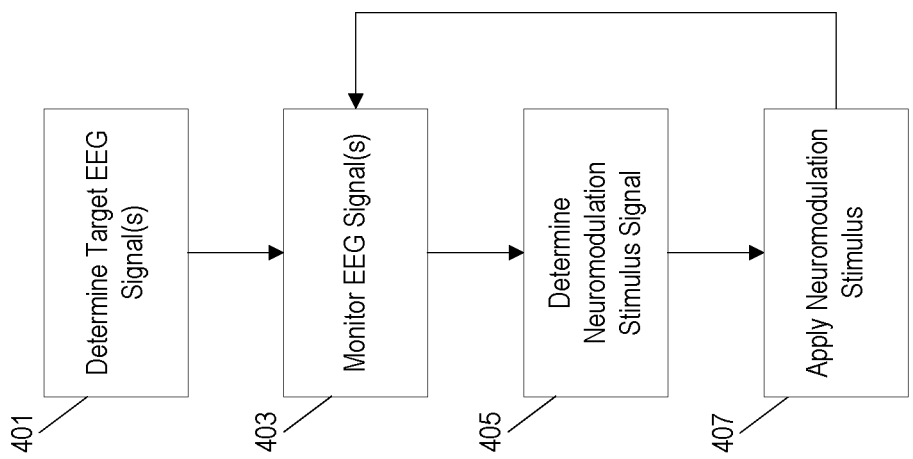
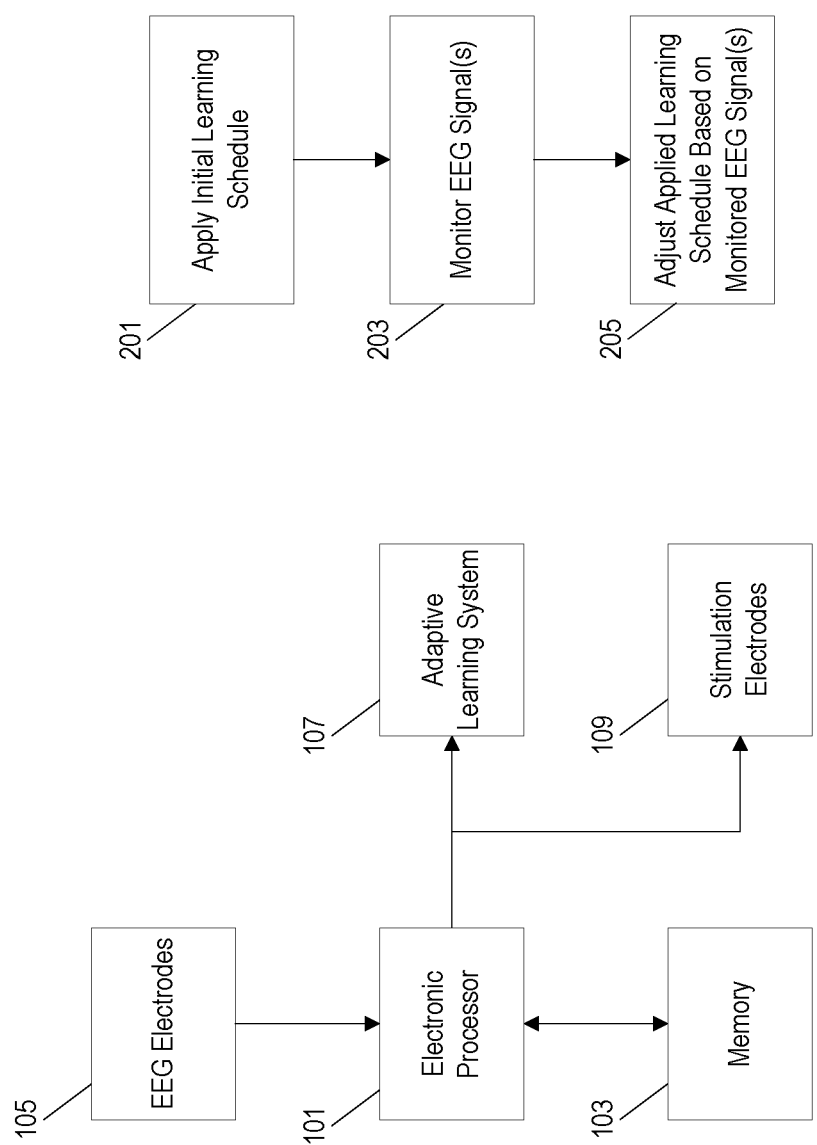

EEG-BASED DECODING AND CLOSED-LOOP NEUROMODULATION SYSTEM FOR ASSESSING AND ENHANCING SENSORIMOTOR LEARNING

RELATED APPLICATIONS

This application claims the benefit of U.S. Provisional Patent Application No. 62/555,488, filed Sep. 7, 2017, entitled "EEG-BASED DECODING AND CLOSED-LOOP NEUROMODULATION SYSTEM FOR ASSESSING AND ENHANCING SENSORIMOTOR LEARNING," the entire contents of which are incorporated herein by reference.

BACKGROUND

The present invention relates to systems and methods for analyzing EEG signal data and for learning sensorimotor tasks.

SUMMARY

Various embodiments and examples described herein are based on two components: (1) non-invasive recording, analysis, and decoding of oscillatory brain activity through scalp electroencephalography (EEG) electrodes, and (2) non-invasive neuromodulation at EEG frequencies related to sensorimotor learning processes. EEG frequencies to be targeted through neuromodulation and timing of neuromodulation delivery are based on a large EEG database built through experiments on sensorimotor adaptation through a wide range of sensorimotor and cognitive motor tasks.

In some embodiments, the invention uses scalp EEG to extract biomarkers that are indicative of sensorimotor learning states and capabilities and, in some embodiments, are used as targets for online neuromodulation to enhance sensorimotor function and skill. This information is combined holistically and hierarchically in an algorithm that uses both the individual's data and normative data collected from others to drive an adaptive learning schedule that is tailored to enhance the individual's learning rate and long-term performance.

In one embodiment, the invention provides a sensorimotor learning system including a plurality of EEG electrodes, an adaptive learning system, and an electronic processor. The adaptive learning system includes an output device (e.g., an audio and/or visual output device). The electronic processor causes the output device to provide a sequence of instructions to the learning subject for performing a sensorimotor task in accordance with a defined learning schedule. The electronic processor also monitors an EEG signal from the plurality of electrodes coupled to the learning subject and adjusts the defined learning schedule based at least in part on the EEG signal.

In another embodiment, the invention provides a method for enhancing sensorimotor learning. A sequence of instructions is provided to a learning subject through an output device. The sequence of instructions instructs the learning subject to perform individual steps of a sensorimotor task according to a defined learning schedule. An EEG signal of the learning subject is monitored while the learning subject performs the sensorimotor task and the defined learning schedule is adjusted based at least in part on the monitored EEG signal.

In still another embodiment, the invention provides a sensorimotor learning system including a plurality of EEG electrodes, a plurality of stimulation electrodes, an adaptive learning system, and an electronic processor. The electronic processor is configured to cause the adaptive learning system to provide a sequence of instructions to a learning subject for performing a sensorimotor task in accordance with a defined learning schedule. The electronic processor monitors an EEG signal while the learning subject performs the task and adjusts the defined learning schedule based on the monitored EEG signal. The electronic processor also determines a neuromodulation stimulus signal that is configured to cause the monitored EEG signal of the learning subject to approach at least one target EEG signal parameter. The neuromodulation stimulus signal is then applied to the learning subject through the at least one stimulation electrode while the learning subject continues to perform the sensorimotor task in accordance with the adjusted defined learning schedule.

Other aspects of the invention will become apparent by consideration of the detailed description and accompanying drawings.

BRIEF DESCRIPTION OF THE DRAWINGS

FIG. 1 is a block diagram of an EEG-based system for assessing and enhancing sensorimotor learning according to one embodiment.

FIG. 2 is a flowchart of a method for adjusting an applied learning schedule for sensorimotor learning using the system of FIG. 1.

FIG. 4 is a flowchart of a method for applying neuromodulation stimulus to enhance sensorimotor learning using the system of FIG. 1.

DETAILED DESCRIPTION

Figure 3:
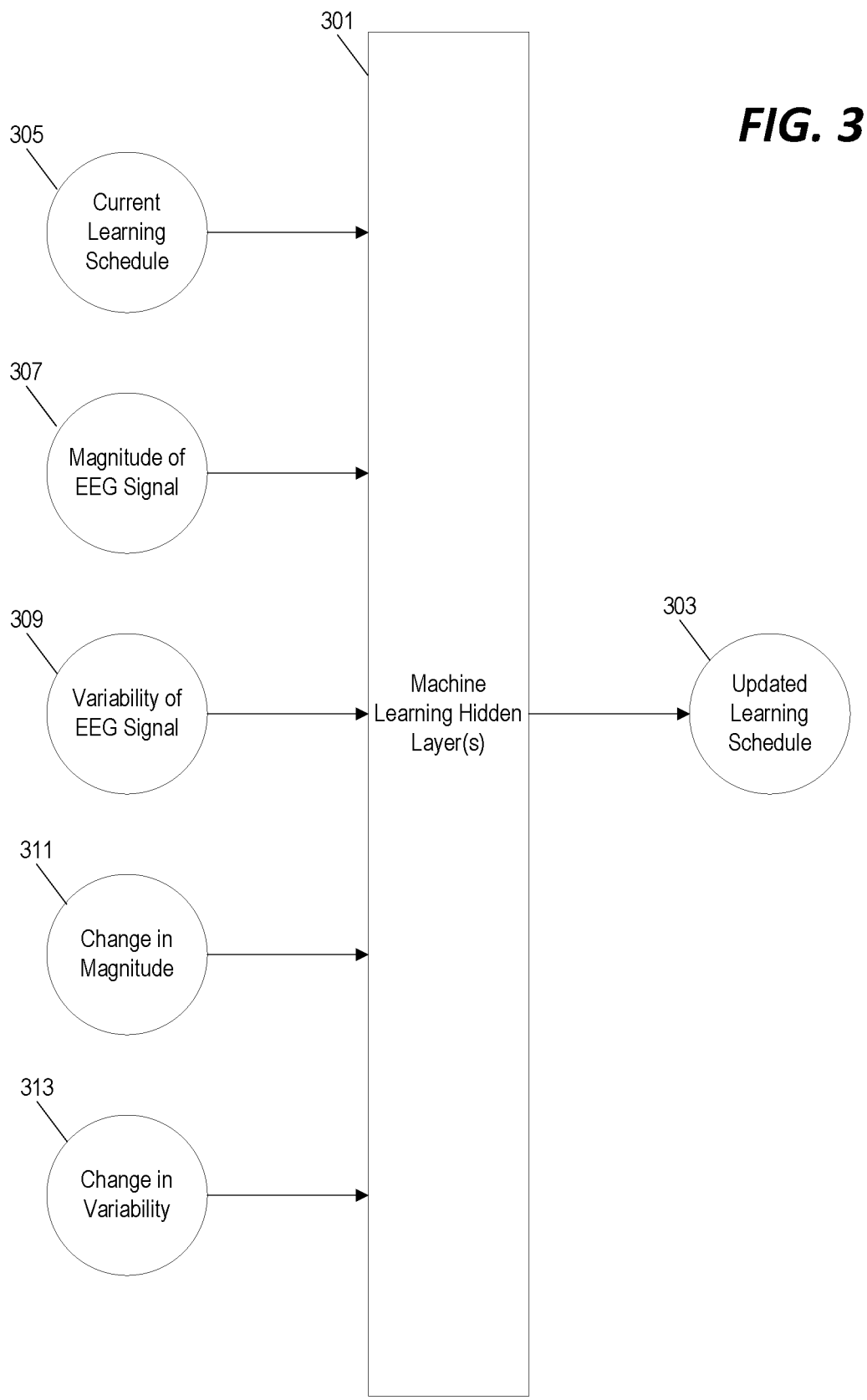
FIG. 3 is a schematic diagram of a machine learning mechanism for use in the method of FIG. 2.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The rate at which humans learn and adapt their movements is adaptive and this adaptive learning can be represented in specific EEG frequencies. Different EEG frequencies are further observed to be associated with distinct sensorimotor learning processes that drive the overall learning rate and quality. Accordingly, the rate at which humans learn new movements may be manipulated through both behavioral and neural intervention. As described in the examples below, particular neural EEG frequencies are used for (1) assessing an individual's sensorimotor capabilities and learning processes, and (2) using the decoded oscillatory information to create a closed-loop system that exogenously enhances the quality of human sensorimotor learning by driving both neuromodulation of ongoing brain activity and driving real-time adaptive changes in learning tasks.

FIG. 1 illustrates an example of a system for assessment and enhancement of sensorimotor learning. The system includes an electronic processor 101 and a memory 103. The memory 103 is a non-transitory computer-readable memory unit that stores instructions which are executed by the electronic processor 101 to provide functionality such as described herein. The electronic processor 101 is communicatively coupled to a plurality of EEG electrodes 105 and is configured to received EEG signal data from the EEG electrodes 105 when they are applied to the scalp of a user.

The electronic processor 101 is also communicatively coupled to an adaptive learning system 107. In some example, the adaptive learning system 107 is an electrical and/or electromechanical system configured to train the user in a sensorimotor task and, in some implementations, to evaluate and measure how well the user performs the sensorimotor task. In other examples, the adaptive learning system 107 may include an audio or visual output system that provides cues or instructions to a user to begin performing a particular task. For example, as discussed in further detail below, the adaptive learning system 107 may be configured to instruct a user when to pick up an object and then records pressures applied to the object as it is held and lifted by the user. In some such implementations, the electronic processor 101 is configured to receive and analyze measured data from the adapted learning system 107 as the object is lifted and is configured to adjust/regulate parameters of the cues/instructions provided to the user including, for example, frequency of the lifting motion and adjustments to the device/context.

In some implementations, the electronic processor 101 is also communicatively coupled to one or more stimulation electrodes or coils 109 and is configured to apply a non-invasive output stimulus to the brain. In some such implementations, the electronic processor 101 is configured to determine one or more target parameters for the EEG signal and then determines and applies a neuromodulation signal designed to invoke the target EEG signal parameters. Although the example of FIG. 1 shows both an adaptive learning system 107 and stimulation electrodes 109, other implementations may include only an adaptive learning system 107 without stimulation electrodes 109 or only stimulation electrodes 109 without an adaptive learning system 107.

FIG. 2 illustrates a method for controlling the adaptive learning system 107 using the system of FIG. 1. First, an initial learning schedule is applied (step 201). As the user performs the task according to the initial learning schedule, the system monitors the EEG signal from EEG electrodes 105 applied to the scalp of the user (step 203). The electronic processor 101 then adjusts the applied learning schedule based at least in part on the monitored EEG signal (or signals) (step 205).

In some implementations, the system of FIG. 1 is configured to apply a machine learning mechanism to determine an appropriate adjustment to the applied learning schedule that would enhance the user's ability to learn and retain the task information based on the monitored EEG signal. FIG. 3 illustrates one such example of a machine learning mechanism. The mechanism includes one or more machine learning hidden layers 301 and outputs an updated learning schedule 303. Various different inputs are provided to the machine learning hidden layer(s) 301. In the example of FIG. 3, the inputs to the machine learning mechanism include a current learning schedule 305, a magnitude of EEG signal 307, a variability of the EEG signal 309, a change in EEG magnitude 311 since the last adjustment of the learning schedule, and a change in EEG variability 313 since the last adjustment of the learning schedule. However, other implementations may be configured to utilize more, fewer, and/or different input parameters.

Furthermore, the ability of the user to learn the task may be evaluated and quantified based on the EEG signal and/or other measurements indicative of the task being performed (e.g., feedback data from the adaptive learning system 107).

In some embodiments, the system is configured to retrain the machine learning model based on this feedback data to further improve the ability of the system to determine an appropriate learning schedule that enhances a user's ability to learn the sensorimotor task. In some implementations, the machine learning hidden layer is trained based only on feedback data from an individual user. However, in other implementations, the machine learning hidden layer is developed, trained, and/or retrained based on feedback information collected from a plurality of users and stored in a database. Accordingly, in some implementations, the electronic processor 101 of the system of FIG. 1 is further configured to collect feedback information regarding the machine learning process and transmit the feedback information to a remote computer system where it is then used to retrain the machine learning model.

As noted above, in some implementations, one or more neuromodulation stimuli is used to enhance the training/learning experience for the user instead of or in addition to feedback-based control of the adaptive learning system. FIG. 4 illustrates one example of a method for applying neuromodulation stimulus/stimuli. First, a target EEG signal and/or EEG signal parameters are determined (step 401). In some implementations, the determined EEG signal and/or signal parameters are indicative of a target learning state (step 401). The system then monitors one or more EEG signals from electrodes applied to the scalp of the user (step 403). The electronic processor 101 then determines a neuromodulation stimulus signal that will cause the monitored EEG signal of the user to approach the target EEG signal parameters (step 405). The neuromodulation stimulus is then applied to the user through the stimulus electrodes 109 (step 407). The electronic processor 101 is configured to repeatedly/continuously monitor the EEG signal and adjust/apply the neuromodulation stimulus to achieve target learning parameters.

In some implementations, the system may also be configured to apply one or more machine learning mechanisms to determine the target EEG signal/parameters and/or the neuromodulation stimulus signal. The machine learning mechanism can be configured to receive various inputs including, for example, parameters of the monitored EEG signal, a target learning state, a current learning state, etc. The machine learning mechanism, in some implementations, is configured, trained, or retrained based on feedback information such as described above in reference to FIG. 3.

The systems and mechanisms described above can be adapted to focus on a number of different EEG signals. However, in the examples described below, the medial frontal e oscillation frequency is predicted by a component of the learning state that adapts to errors based on a context switch (i.e., a change in the sensorimotor task being learned). In contrast, somatosensory and visual ($\alpha$) and motor ($\beta$) cortex signals are predicted by a learning state that is updated from performance errors independent of a learning context. The system (such as, for example, illustrated in FIG. 1) can be adapted to utilize these frequencies as biomarkers to be extracted during execution of simple learning tasks to quantify an individual's abilities to adapt sensorimotor skills and compare to normative data. These learning tasks include adaptation to perturbations and sequence learning. These neural frequency data, behavioral performance, and computational learning model data are combined into a statistical neural network predictive model (as discussed above in reference to FIG. 3). Potential diagnostic applications include, but are not limited to, diagnostics of sensorimotor function following traumatic injury (e.g., traumatic brain injury) and/or neurodegeneration (e.g., Parkinson's disease, Alzheimer, stroke). The EEG oscillatory biomarkers, computational learning process data, and predictive neural network model data that are extracted are then used to enhance further learning. This enhancement is done both by (1) non-invasive neuromodulation at each specific frequency and cortical site, and (2) using the pre-measured cortical frequency information to drive a machine learning algorithm that controls an adaptive learning schedule in terms of magnitude and variability of perturbations. This informed algorithm is used to influence a specific learning component in an online, closed-loop fashion as an individual performs the sensorimotor learning task (or tasks).

When movements are adapted to one perturbation through errors, e.g., force fields, visuomotor rotations, or a novel object's dynamics, then subsequently adapted to an opposite perturbation, adaptation to the first context interferes with adapting to the second. This phenomenon is often evidenced by slower adaption to the second perturbation compared to the first context, i.e., anterograde interference. This observation is thought to arise from the motor memory for the first context competing with learning of the second context, wherein adaptation to the second context is assumed to overwrite adaptation to the first context.

Thus, the invention provides, among other things, a system and method for assessing and enhancing sensorimotor learning using EEG signal data. Various features and advantages of the invention are set forth in the following claims.

What is claimed is:

1. A sensorimotor learning system, the system comprising:
    a plurality of EEG electrodes selectively couplable to a learning subject;
    a plurality of stimulation electrodes selectively couplable to the learning subject;
    an adaptive learning system including an output device configured to provide at least one output selected from a group consisting of a visual output and an audio output; and
    an electronic processor configured to
        cause the output device of the adaptive learning system to provide a sequence of instructions to the learning subject for performing a sensorimotor task in accordance with a defined learning schedule,
        monitor an EEG signal from the plurality of EEG electrodes,
        adjust the defined learning schedule based on the monitored EEG signal,
        determine a neuromodulation stimulus signal based on the monitored EEG signal and at least one target EEG signal parameter, wherein the neuromodulation stimulus signal is determined to cause the monitored EEG signal to approach the at least one target EEG signal parameter; and
        apply the neuromodulation stimulus signal to the learning subject through the at least one stimulation electrode while the learning subject performs the sensorimotor task in accordance with the adjusted defined learning schedule.

2. The sensorimotor learning system of claim 1, wherein the electronic processor is configured to adjust the defined learning schedule by adjusting a frequency at which instructions in the sequence of instructions are output by the output device of the adaptive learning system.

3. The sensorimotor learning system of claim 1, wherein the electronic processor is configured to monitor the EEG signal by determining a change in a magnitude of the EEG signal since a previous adjustment of the learning schedule.

4. The sensorimotor learning system of claim 1, wherein the electronic processor is configured to monitor the EEG signal by determining a change in a variability of the EEG signal since a previous adjustment of the learning schedule.

5. The sensorimotor learning system of claim 1, wherein the electronic processor is configured to adjust the defined learning schedule by applying a machine learning mechanism.

6. The sensorimotor learning system of claim 5, wherein the electronic processor is configured to apply the machine learning mechanism by
    providing a plurality of inputs to a neural network, the plurality of inputs including the defined learning schedule, a magnitude of the EEG signal, a variability of the EEG signal, a change in the magnitude of the EEG signal since a previous adjustment to the learning schedule, and a change in the variability of the EEG signal since the previous adjustment to the learning schedule, and
    receiving an updated learning schedule as an output of the neural network.

7. The sensorimotor learning system of claim 5, wherein the electronic processor is further configured to
    receive, through the adaptive learning system, at least one metric indicative of a proficiency with which the sensorimotor task is being performed, and
    retrain the machine learning mechanism based at least in part on the at least one metric indicative of the proficiency.

8. The sensorimotor learning system of claim 7, wherein the adaptive learning system includes at least one sensor configured to generate a signal indicative of the sensorimotor task being performed by the learning subject, and wherein the electronic processor is configured to determine the at least one metric indicative of the proficiency based at least in part on the signal from the at least one sensor of the adaptive learning system.

9. The sensorimotor learning system of claim 5, wherein the electronic processor is further configured to
    compare the EEG signal to the at least one target EEG signal parameter, wherein the at least one target EEG signal parameter is indicative of a target learning state, and
    retrain the machine learning mechanism based at least in part on a difference between the EEG signal and the at least one target EEG signal parameter.

10. The sensorimotor learning system of claim 9, wherein the at least one target EEG signal parameter includes a medial frontal oscillation frequency.

11. The sensorimotor learning system of claim 1, wherein the EEG signal includes at least one selected from a group consisting of a medial frontal EEG signal, a visual cortex EEG signal, and a motor cortex EEG signal.

12. A method for sensorimotor learning, the method comprising:
    providing a sequence of instructions to a learning subject through an output device, the sequence of instructions instructing the learning subject to perform individual steps of a sensorimotor task according to a defined learning schedule;
    monitoring an EEG signal from a plurality of electrodes affixed to the head of the learning subject;

adjusting the defined learning schedule based at least in part on the monitored EEG signal;

determining a neuromodulation stimulus signal based on the monitored EEG signal and at least one target EEG signal parameter, wherein the neuromodulation stimulus signal is determined to cause the monitored EEG signal to approach the at least one target EEG signal parameter; and applying the neuromodulation stimulus signal to the learning subject through at least one stimulation electrode while the learning subject performs the sensorimotor task in accordance with the adjusted defined learning schedule.

13. The method of claim 12, the method further comprising:

providing a plurality of inputs to a neural network, the plurality of inputs including the defined learning schedule and at least one parameter of the monitored EEG signal; and receiving an updated defined learning schedule as an output of the neural network, wherein adjusting the defined learning schedule includes providing the sequence of instructions to the learning subject through the output device according to the updated defined learning schedule.

14. The method of claim 13, further comprising retraining the neural network based on a difference between the monitored EEG and at least one target EEG signal parameter.

* * * * *